United States Patent [19]

Ceriani et al.

[11] Patent Number: 4,584,268

[45] Date of Patent: Apr. 22, 1986

[54] METHOD AND COMPOSITIONS FOR CARCINOMA DIAGNOSIS

[76] Inventors: Roberto L. Ceriani, 1089 Via Roble, Lafayette, Calif. 94549; Jerry A. Peterson, 5916 Chabot Rd., Oakland, Calif. 94618

[21] Appl. No.: 583,456

[22] Filed: Feb. 24, 1984

Related U.S. Application Data

[63] Continuation of Ser. No. 310,952, Oct. 18, 1981, abandoned.

[51] Int. Cl.$^4$ .................... G01N 33/54; G01N 33/56; B65D 71/00
[52] U.S. Cl. ........................................ 435/7; 436/504; 436/518; 436/528; 436/537; 436/542; 436/800; 436/804; 436/808; 436/813; 422/61; 260/112 R; 260/112 B
[58] Field of Search ................ 424/1, 1.5; 260/112 R, 260/112 B; 436/504, 518, 528, 537, 542, 543, 547, 800, 804, 813

[56] References Cited

U.S. PATENT DOCUMENTS

| | | | |
|---|---|---|---|
| 3,979,507 | 9/1976 | Baker | 424/1.5 |
| 4,229,426 | 10/1980 | Haagensen, Jr. | 424/1 |
| 4,232,001 | 11/1980 | Jensen et al. | 424/1 |
| 4,311,688 | 1/1982 | Burchiel et al. | 424/1.5 |
| 4,331,647 | 5/1982 | Goldenberg | 424/1 |

OTHER PUBLICATIONS

Sebesteny et al., J. Natl. Cancer Inst., 63 (1979), 1331–7.
Sloan et al., Cancer 47:1786–1795 (1981).
Lipinski et al., Proc. Natl. Acad. Sci. USA 78:5147–50 (1981).
Nadler et al., J. Clin. Invest. 67:134–140 (1981).
Priori et al., J. Natl. Cancer Inst. 48:1131–1135 (1972).
Richman, J. Natl. Cancer Inst. 57:263–267 (1976).
Chiu et al., J. Natl. Cancer Inst. 59:151–154 (1977).
Schlom et al., Proc. Natl. Acad. Sci. USA 77:6841–45 (1980).
Colcher et al., Cancer Res. 41:1451–57 (1981).
Colcher et al., Proc. Natl. Acad. Sci. USA 78:3199–03 (1981).
Edynak et al., J. Natl. Cancer Inst. 48:1137–43 (1972).
Weisz–Carrington et al., J. Immunol. 119:1306–1309 (1977).
Irie et al., Science, 186:454–456 (1974).

*Primary Examiner*—Christine M. Nucker
*Attorney, Agent, or Firm*—Bertram I. Rowland

[57] ABSTRACT

Methods and compositions are provided for detecting the presence of carcinomas in a mammalian host by measuring the level of normal surface antigens specific for a differentiated cell in the serum of the host as compared to the normal level of such antigen. The method finds particular use in detecting residual carcinomas after therapy or in detecting the recurrence of neoplastic tissue, and assigning a tissue of origin to the neoplastic tissue.

16 Claims, No Drawings

METHOD AND COMPOSITIONS FOR CARCINOMA DIAGNOSIS

This invention was made with U.S. Government support under Grant No. R01-CA-20-286 awarded by the National Institutes of Health. The U.S. Government may have certain rights in this invention.

CROSS-REFERENCE TO RELATED APPLICATIONS

This is a continuation of application Ser. No. 310,952, filed Oct. 18, 1981 now abandoned.

BACKGROUND OF THE INVENTION

1. Field of the Invention

Numerous markers have been suggested to assess the prognosis or monitor the continued presence of carcinomas in a mammalian host. As illustrative, for human breast carcinomas, calcitonin, carcinoembryonic antigen (CEA) and its related materials, ferritin, transferases and milk proteins have been suggested. None of them has found acceptance as a specific sensitive breast tumor marker to be used in clinical management of the disease.

There are many situations in the diagnosis and treatment of cancer in mammals where a reliable test having a low level of false negatives would be extremely valuable by itself and particularly in conjunction with other tests, such an imaging. Desirably, the test should be relatively simple and accurately and reliably measure the diagnostic marker in the range of interest.

2. Description of the Prior Art

Mammary tumor cell surface antigens have been identified in the sera of rats with mammary carcinomas. (Ghosh et al., (1979) J. Natl. Cancer Inst. 62:1229-1233). Some of these membrane fragments appear to be antigenic to the patient and may exist as free antigens or together with the corresponding specific antibodies as circulating, soluble immune complexes in circulation. Hoffken et al., (1977) Br. Med. J. 2:218-220); Kim et al., (1975) PNAS U.S.A. 72:1012-1016). The isolation and characterization of normal human mannary epithelial antigens prepared from human milk fat globules has been reported. Ceriani et al., (1979), In: Boelsma E., Rumke P. eds. Applied Methods in Oncology. Amsterdam: Elsevier, 101-116; Ceriani et al., (1977) PNAS U.S.A. 74:582-586; Ceriani et al., (1980) In: Mcgrath C. ed. Workshop Processings "Systematic of Breast Cell Transformation." New York: Academic Press, 3356 and Peterson et al., (1978) Int. J. Cancer 22:655-661. See also U.S. Pat. No. 3,979,507 and references described therein.

SUMMARY OF THE INVENTION

Methods and compositions are provided for detecting the presence of neoplastic tissue in a mammalian host and determining the tissue of origin of such neoplastic tissue. Serum is monitored for the presence of normal surface antigens specific for differentiated cells in patients suspected of having a cancer of that cell type. Receptors, normally antibodies, specific for a plurality of determinant sites associated with normal surface antigens specific for differentiated cells are employed to measure the levels of such specific antigens in the host suspected of having a solid primary tumor and/or metastases, in comparison to the normal level of such surface antigens in circulation. Any convenient diagnostic assay specific for the determinant sites may be employed, particularly competitive protein binding assays, having the necessary sensitivity for detecting the antigen in the range of interest.

DESCRIPTION OF THE SPECIFIC EMBODIMENTS

The subject invention provides a method for determining the presence of solid tumors and/or metastases in a mammalian host, indicating not only the presence or absence of neoplastic tissue but also the nature or source of the neoplastic tissue. Various mammalian hosts may be diagnosed, such as research animals, domestic animals, pets and humans. A serum sample is employed and the presence of an elevated concentration of normal surface antigen associated with cells from non-circulating normal tissue is determined. That is, the surface antigens can be specific for a number of different structural organs. The organs of interest may be encased in facius membrane. Monitoring is solely for the surface antigen and not for other antigenic materials which may be associated with the differentiated cell.

Illustrative organs of interest include the breast, prostate, colon, bladder, heart, kidney, lung, brain, muscle, nerves, etc. Those organs of particular interest are those where the cells either do not regenerate or have only slow regeneration.

The concentration level of at least one surface antigen in serum is determined and compared to the normal level of such surface antigen. The surface antigen may be free of other materials, may be a fragment of a surface antigen, or may be part of a cell membrane associated with other surface antigens. Particularly, the surface antigen will be a normal surface antigen associated with the differentiated cell, usually a mature cell. The presence of the surface antigen may be detected by receptors specific for one or more determinant sites, either sites which are exposed while the antigen extends into the membrane or sites which become exposed when the surface antigen is freed from the membrane. Normally, it will be desirable to detect more than one determinant site, usually two or more determinant sites, particularly determinant sites on different surface antigens specific for the differentiated cell, more preferably two or more determinant sites on each of two or more surface antigens specific for the differentiated cell of interest. By demonstrating that two or more antigens specific for the differentiated cell of interest have elevated concentration in circulation, greater confidence in the existence of neoplastic tissue is adhieved and recognition of the type of tissue of origin that releases the antigen.

While any receptor may be employed which is specific for the determinant sites of interest, for the most part the receptors will be antibodies, either polyclonal or monoclonal, and while any immunoglobulin may be employed, for the most part IgG will be employed. Either whole antibodies or fragments thereof, e.g. $F(ab')_2$ Fab, $F_d$ or $F_v$. As indicated, while single monoclonal antibodies may be employed, for the most part mixtures of antibodies will be employed, including mixtures of monoclonal antibodies or mixtures of polyclonal antibodies. The number and type of antibodies which are employed will depend upon the number of determinant sites and number of different surface antigens which are to be measured. The antibody composition will be free of antibodies specific for antigens other than the specified surface antigens.

The differentiation surface antigen can be detected by preparing antibodies to the cell, cell membrane, or surface antigens of interest and then screening against a number of different cells from other tissue. Particularly, one can screen the antibodies by combining them with surface antigens or cell membranes from a variety of cells different from the cell of interest, particularly where the surface antigens and cells are bound to a support allowing for ready separation between antibodies which do not bind and antibodies which do bind. One can then further purify the antibodies by combining them with surface antigens from the cell of interest which are bound to a support and then releasing the antibodies by employing various solutions, such as sodium isocyanate or acetic acid at a concentration sufficient to break down the antigen-antibody complex.

The particular manner in which the presence of the surface antigens is detected is not significant in this invention, so long as the method provides the desired degree of sensitivity and reliability. A number of different types of immunoassays exist having a variety of protocols and labels. For the most part, the commonly available assays for detecting specific determinant sites are competitive protein binding assays or immunoassays, where antibodies or fragments thereof are employed.

Competitive protein binding assays are divided into two categories, heterogeneous, which involves a separation step between bound label and unbound label, where the bound label is involved with an antigen-antibody complex, or homogeneous, where the signal from the label varies between being bound or unbound in an antigen-antibody complex. In the heterogeneous assay, either the antigen or the antibody is normally bound to a support to permit ready separation. The support may be a particle, a container surface e.g. the wall of a microtiter plate well, a chromatographic plate, or the like. Either the surface antigen may compete with labelled antigen for a limited amount of antibody or more commonly, the antigen may serve as a bridge between antibody bound to a support and labelled antibody (pseudo-competitive). Various labels include radionuclides, enzymes, fluorescers or the like.

Homogeneous assays do not involve a separation steps, but rely on the fact that one can distinguish between the signal obtained from a label when the label is involved with an antigen-antibody complex and when the labelled member of the binding pair is not bound to its complementary member to form a complex. These assays include as labels enzymes, fluorescers, and enzyme substrates or inhibitors.

As illustrative of the various homogeneous and heterogeneous assays, are assays described in U.S. Pat. Nos. 3,646,346; 3,791,392; 3,817,837; 3,935,074; 3,867,517; 3,996,345; 4,230,797; 4,233,402; and 4,275,149.

Other assays which are not considered competitive or pseudo-competitive protein binding assays, are such assays which depend upon the precipitin reaction or hemeagglutination. Descriptions of these tests may be found in U.S. Pat. Nos. 3,171,783; 3,457,344; and 3,892,841.

In view of the wide diversity of protocols depending upon the particular label, the specific protocols will not be described. Common to the assays is the formation of a reagent solution containing labelled antibody or labelled antigen, normally labelled antibody in the heterogeneous assays, while either labelled antibody or labelled antigen may be employed in the homogeneous assays. The reagent solution will contain in addition to the labelled component, other additives, such as buffers e.g. phosphate, tris, barbital, or the like, normally at concentrations in the range of about 0.01 to 1 mM, the concentration being sufficient to maintain a pH in the range of about 6.5 to 9, more usually 7 to 8 during the assay. Other additives include preservatives e.g. sodium azide, inert protein e.g. serum albumin, sodium chloride, detergents, or the like, which aid in preserving the labelled component, enhancing the formation of the antigen-antibody complex, preventing non-specific binding, or unlabelled component, or the like.

The concentrations of interest will vary depending upon the nature of the particular organ of interest. Normally, the concentration observed should be at least 50% greater than the normal concentration, when there is a normal concentration, more usually at least twice the normal concentration, and desirably at least 3 times the normal concentration. Usually, the concentration will be at least about 10 pg/ml, more usually at least 1 ng/ml and preferably at least about 100 ng/ml.

Where the normal amount of surface antigen diagnostic for cancer is undetectable, the following technique may be employed for establishing the presence of the surface antigen in serum. The qualitative method involves combining serum with antibodies specific for the surface antigen bound to a solid support, so that any surface antigen present becomes bound to the support through the intermediary of an antigen-antibody complex. The solid support is then separated from the liquid phase and the protein bound to the support labelled with any convenient label e.g. a radionuclide. Any bound surface antigen is released from the complex and then separated into constituent fractions, if any, by electrophoresis, chromatography, gradient density centrification or the like. The bound antigens may be detected by means of the label and may be compared with an authentic sample of the surface antigen or further characterized.

There will be a variety of situations where the serum of a host will be measured for detection of the presence of neoplastic tissue. In the original diagnosis, where a host is suspected of having a neoplasm, the serum may be screened for surface antigens of the particular tissue which is suspected of having developed a neoplasm. This test can be used in conjunction with other tests, to enhance the confidence level of the presence of a carcinoma. Where a carcinoma has been detected and removed, the presence of residual neoplastic tissue or metastases may be determined. In addition, where a mass is found suggestive of a metastasis of unknown origin, the origin can be determined by employing antibodies specific for different types of tissue. Furthermore, the clinical applications include the detection of residual tumor masses (local or metastatic) after therapy and in the follow-up for recurrence after the neoplastic tissue has been eradicated.

The labelled antibodies will normally be supplied as a lyophilized powder in combination with conventional stabilizers and other additives, including buffers, neutral salts, bulking agents, inert proteins, detergents e.g. non-ionic detergent and other additives associated with the nature of the label, e.g. substrates for enzyme. These additives will be present in varying amounts with the antibodies being present in about 0.005 to 5 weight percent, preservatives in about 0.001 to 1 weight percent, neutral salt in about 0 to 15 weight percent, protein in about 0 to 10 weight percent and the remainder bulking agent. The labelled antibody will normally be combined with various excipients, which may serve as extenders and aid in handling and stabilization of the labelled antibody.

Usually, the labelled antibodies will be provided as a kit in combination with controls to produce a standard curve. The controls will have the surface antigen usually formulated with minor amounts of additives, such as inert protein, non-ionic detergents e.g. Triton X-100, buffer, preservations, or the like. Also included will be bulking agents e.g. mannitol. The minor additives will range from about 0.001 to 2 weight percent. The antigen will be present in varying amounts to provide the desired concentration on dissolution into a prescribed volume.

In some instances, labelled surface antigen will be employed, where the labelled surface antigen may be formulated the same or similar way as the labelled antibody.

The following examples are offered by way of illustration and not by way of limitation.

EXPERIMENTAL

Nude Mouse Colony

Nude mouse of the BALB/c background (nu/nu) were from the nude mouse colony at the University of Califorina, San Francisco. The colony was developed by breeding of heterozygous females with nude homozygous males and maintained in rigid isolation with a filtered air supply under positive pressure. The animals were handled in aseptic conditions with sterilized bedding, cages and food and used for tissue implantation 6 to 8 weeks after birth.

HME-Ags and Antibody Production

Human mammary epithelial antigens (HME-Ags) were prepared from a membrane fraction of delipidated human milk fat globules (HMFG) as described in Ceriani et al., (1977). Anti-human mammary epithelial (anti-HME) antibody was produced in rabbits and rendered HME-specific by sequential absorption with human blood cells, human colon carcinoma cells (cell line HT-29), and human cervical carcinoma (HeLa cells) (Peterson et al., (1978), supra).

Implantation of Tumors

Transplantable human breast tumor MX-1 (primary carcinoma), colon carcinoma CX-1 lung carcinoma LX-1, and the Wilson melanoma were all provided by Dr. A. E. Bogden, EG & G Mason Research Institute, Worcester, Mass. The MX-1, CX-1, LX-1, and Wilson melanoma were originally established by Dr. B. Giovanella, Stehline Foundation, St. Joseph Hospital, Houston, Tex. and had been passed 24, 4, 36, and 10 times, respectively, in nude mice when received. A transplantable medulloblastoma tumor line was provided by Dr. W. Wara, Department of Radiation Oncology, University of California. For transplantation, pieces of these tumors were put into Waymouth's medium after removal and further cut into small pieces (2-4 mm in diameter) and 1-2 such fragments were implanted subcutaneously in the thigh area of the animals. Only female mice were selected for implantation of breast tumor tissues.

Sampling of Blood Plasma

Tumors became palpable usually three to four weeks after implantation. When the tumor reached 10 mm in diameter or larger, it was removed surgically. Care was taken to remove malignant tissues as completely as possible; 200-300 $\mu l$ of blood was withdrawn for the periobital venous plexus with a heparinized capillary tube. Animals with breast tumors were bled twice before the tumor removal, first between 7 and 4 days before and then a second time between 3 days and on the day of tumor removal. Animals with non-breast tumors were bled once between 3 days before and on the day of removal. In all animals, postoperative blood samples were taken between 3 to 7 days after the tumor removal.

Histology of Tumor Tissues Grown in the Nude Mice

For histologic examination, the excised tissues were fixed in buffered 10% formalin solution, dehydrated with an ethanol series and embedded in paraffin. Paraffin sections (8-10 $\mu m$) were cut and stained with hematoxylin:eosin. Portions of the breast tumors were also processed for indirect immunofluorescent test to identify HME-Ags as has been described in detail (Ceriani et al., (1977), supra.).

RIA of HME-Ags

Preparation of anti-human mammary epithelial (anti-HME) antibody and iodination of HMFG with a modified chloramine-T method have been reported (Ceriani et al., (1977) supra). The HMFG standard antigen stock solution (100 $\mu g/ml$ of RIA buffer; 0.5% bovine serum albumin, 0.3% Triton X100, and 0.05% sodium azide in phosphate buffered saline, pH 7.2) was sonicated with a Biosonic sonicator (Bronwill Scientific, Rochester, N.Y.) with five 15-second bursts interspersed with 15-second standing periods on ice. To construct a standard competition curve, polystyrene tubes (Pharmacia Diagnosis, Piscataway, N.J.) received, in triplicate, 0.1, 0.3, 1, 3, 10, 30, 100, and 300 ng of solubilized HMFG solution in a volume of 20 $\mu l$. To quantitate the HME-Ags in nude mouse plasma, 20 $\mu l$ of each plasma were placed, in triplicate, into incubation tubes. To compensate the effects of plasma in the unknown sample, 20 $\mu l$ of plasma from BALB/c female mouse and of the Simonsen strain were included in all standard competition tubes.

Standard and unknown plasma samples were incubated with 30 $\mu l$ of anti-HME antibody (usually in a $3 \times 10^3$-fold dilution) and 200 $\mu l$ of RIA buffer at 20° C., 5-6 hr. with constant agitation (100 rpm, Gyratory Shaker, New Brunswick Scientific Co., Inc., New Brunswick, N.J.). This amount of anti-HME antibody was determined, each time $^{125}I$-labeled antigen was prepared, to be sufficient to bind 40-50% of the maximum immunoprecipitable counts in the present RIA system. Then 10 $\mu l$ of $^{125}I$-HMFG solution (30-40$\times 10^3$ cpm) were added to each tube which was further incubated overnight at 20° C. Finally, 30 $\mu l$ of Protein A-bacterial-cell-suspension (10%, v/v in RIA buffer), which was prepared from Staphylococcus aureus, Cowan I, according to Kessler, (1976) J. Immunol. 117:1482-1490, were added to each tube which was then allowed to stand for 60 min. at 20° C. and centrifuged at 1000 g for 10 min. The supernatant fractions were carefully removed and cell pellets washed twice with 5 ml of PBS and their radioactivity counted in a Packard gamma scintillation spectrometer.

Statistical Analysis

Assessment of diagnostic sensitivity and specificity, predictive value and cutoff value were evaluated according to Statland et al., In: Henry J. B. ed., Clinical diagnosis and management by laboratory methods, Philadelphia: W. B. Saunders Co. 1979:525–523. The effect of tumor removal on the level of HME-Ags in the nude mounse plasma was analyzed using a paired t test. Huntsherger and Billingsley, Elements of Statistical Analysis, 3rd ed. Boston: Allyn and Bacon, Inc., 1973:176–198.

A typical standard competition curve for RIA which was performed which showed the competition between HMFG with $^{125}$I-labeled HME-Ags at a level as low 0.5 ng. The most sensitive range found was normally between 0.5 and 10 ng in most competition curves. The plasma sample of volume employed was 20 $\mu$l, so that the minimal statistically significant measureable value of the HME-Ags was around 25 ng/ml of plasma and any values less than 30 ng/ml were regarded as background values.

The levels of plasma HME-Ags in individual nude mice emplanted with various human tumors were determined before and after surgical removal of tumor tissues (Table 1).

TABLE I

Comparison of Levels of Plasma HME-Ags before and after Surgical Removal of Breast and non-Breast Tumors in Nude Mice (ng/ml)

| Human tumor grafted | No.* | Tumor Removal Before | After |
|---|---|---|---|
| Breast carcinoma | (12) | 687 ± 184+ | 82 ± 33 |
| Colon carcinoma | (8) | 50 ± 29 | 33 ± 23 |
| Lung carcinoma | (5) | 82 ± 78 | 64 ± 28 |
| Medulloblastoma | (5) | <30 | <30 |
| Wilson melanoma | (5) | <30 | <30 |
| Control | (11) | 49 ± 22 | |

*Numbers of nude mice sampled for each tumor.
+Mean ± SE

In animals with the breast tumor, the plasma levels before tumor removal were expressed as a mean of two separate samples obtained at the different times. Of twelve animals with breast tumors, eight animals showed HME-Ags levels of more than 300 ng/ml. The mean standard error (SE) in this group was 687±184 ng/ml and 82±38 ng/ml before and after the tumor removal, respectively. The difference of the HME-Ags levels in this group before and after the operation was statistically significant at the 1% level when they were compared by the paired t-test. The levels of plasma HME-Ags in animals with non-breast tissues, on the other hand, did not change significantly after the tumor excision ($P>0.05$). None of the latter animals exceeded HME-Ags levels of 300 ng/ml. Control animals from the colony employed, heathly female nude mice with no tumors, gave HME-Ags levels of 49±22 ng/ml, which is statistically different from those of any non-breast tumor animals ($P>0.05$).

Changes in HME-Ags levels before and after tumor removal in individual animals with a breast tumor were monitored. Of twelve animals in the group, all animals except one dropped their antigen level below 200 ng/ml within 3–4 days after resection of tumors. A drastic drop was observed in seven animals (a drop of more than 500 ng/ml), a moderate drop in three animals (a range: 300–100 ng/ml) and the remaining two animals did not show any significant change. These last two animals had very low antigen levels (less than 100 ng/ml) even while they carried the breast tumors and maintained these low levels after tumor resection. In one animal with breast tumor, the level of HME-Ags was high (450 ng/ml) in the plasma even after removal of the tumor.

Human breast cancer patients were monitored with an RIA employing reagents prepared as follows. An aqueous solution of 3 mg anti-HME, 0.5 M NaCl, 100 mM NaHCO$_3$ was mixed with 1 ml swollen cyanogen bromide-activated Sepharose-4B beads (Pharmacia), the beads being washed for 15 min in 1 mM HCl before use. After agitating the mixture for 2–3 hrs at room temperature, the beads are washed in the above buffer, followed by incubation in 0.2 M glycine buffer, pH 8.0, for 2 hrs, followed washing 3×X with the carbonate buffer and stored in 0.01 M sodium azide PBS at 4° C.

Anti-HME was iodinated with 1 mCi of carrier-free $^{125}$I as described above.

In the assay 0.1 ml of anti-HME coated beads in PBS (0.05 M KNaHPO$_4$, pH 7.4, 0.15 M NaCl is added to 0.5 ml of human serum and agitated in the presence of 0.01 M NaN$_3$ at room temperature overnight. To avoid proteolysis 0.1 mM phosphomonosulfonyl fluoride and 1 mM $\epsilon$-aninocaprioc acid. After the overnight incubation, the beads are thoroughly washed, incubated with $10^6$ cpm of $^{125}$I labelled anti-HME in PBS, 0.01 M NaN$_3$, with continuous agitation for 6 hrs. After washing the beads several times with PBS, the beads are counted in a gamma counter. Standard curves are prepared using varying amounts from 0.05 ng to 100 $\mu$g of dissolved human milk fat globule.

By comparing sera from normal individuals, sera of patients with disseminated cancer other than breast, and sera of patients with small primary lesions were not statistically different from each other, while breast cancer patients with disseminated disease showed statistically significant elevated values over the controls. A more sensitive assay would be anticipated to be able to detect the primary lesions of breast cancer.

To further establish that HME surface antigen was involved, the beads and breast cancer patient serum was combined as described above, followed by labelling the complex with $^{125}$I, as described above, and then releasing the $^{125}$I labelled antigen with 2 M sodium isothiocyanate. The released antigen is dialyzed against PBS, concentrated, electrophoresed in polyacylamide gel (Laemmli (1970) Nature 227:680–685). The labelled antigen was shown to correspond to HME-Ags previously described. (Ceriani et al. (1977) PNAS U.S.A. 74:582–586; Sasaki et al. (1981) In Vitro 17:150–158).

The antigens include three components of molecular weights 48,000, 75,000 and 150,000.

In accordance with the above results, HME-Ags in sera are specifically identified with the presence of human breast cancer and/or its metastases.

In accordance with the subject invention, it has been shown that the presence of plasma HME-Ags in nude mice implanted with human breast tumors and background levels of these antigens in animals with non-breast tumors and healthy animals indicate that animals with breast tumors do release into the blood HME-Ags which are found in the membrane components of HMFG. In addition, a drastic drop of the antigen level after the surgical removal of a breast tumor strongly supports the fact that the level of the circulating antigens is directly associated with the presence or absence of the human breast tumor in the host. The drastic drop of HME-Ags levels 3–4 days after resection of the human breast tumor indicates that circulating antigens appeared to be cleared rapidly from circulation once the tumor is removed.

The assays according to this invention are therefore valuable in the confirmation of breast cancer in a patient, particularly in combination with other diagnostic means, as well as in cases where a mass is found suggestive of a metastasis of unknown origin. By employing various antibodies to surface antigens specifically associated with mature differentiated cells, the origin of the metastasis may also be determined. Furthermore, the subject method finds application in the detection of residual tumor masses (local or metastatic) after therapy of the primary tumor and the follow-up for recurrence after neoplastic tissue has been eradicated.

Although the foregoing invention has been described in some detail by way of illustration and example for purposes of clarity of understanding, it will be obvious that certain changes and modifications may be practiced within the scope of the appended claims.

What is claimed is:

1. An assay method for detecting the presence of neoplastic mammary epithelial tissue from a solid tumor or metastasis of a mammary organ of a mammalian host which comprises:
    combining a serum or plasma sample of said host with antibodies specific for at least one surface antigen specific for a normal differentiated epithelial cell of said mammary organ, wherein any of said surface antigen present in said serum or plasma binds to said antibodies to form an antigen-antibody complex;
    determining the amount of said complex; and
    comparing the amount of said complex in said serum or plasma with the amount of complex in a mammalian host free of neoplastic tissue of said mammary organ.

2. A method according to claim 1, where a competitive or pseudo-competitive protein binding assay is employed for said assay.

3. A method according to claim 2, wherein said assay is a radioimmunoassay.

4. A method according to claim 2, wherein said assay is an enzyme immunoassay.

5. A method according to claim 4, wherein said enzyme immunoassay is a heterogeneous immunoassay.

6. A method according to claim 4, wherein said enzyme immunoassay is a homogeneous immunoassay.

7. A method according to claim 2, wherein said assay is a fluorescent assay.

8. A method for detecting the presence of neoplastic tissue from a solid tumor or metastasis of a mammary organ of a mammalian host which comprises:
    combining serum from said host with antibodies bound to a support, wherein said antibodies are specific for at least one surface antigen specific for a normal differentiated epithelial cell of said mammary organ, wherein any of said surface antigen present in said serum binds to said antibodies to form an antigen-antibody complex;
    adding labelled antibodies specific for said surface antigen which bind to said surface antigen in said antigen-antibody complex to form a sandwich;
    separating said support from any liquid; and
    determining the amount of label bound to said support as compared to the amount of label bound to said support in the presence of a known amount of said surface antigen.

9. A method according to claim 8, wherein said label is a radionuclide.

10. A method according to any of claims 8 or 9, wherein said organ is the breast.

11. A method for detecting the presence of neoplastic tissue from a solid tumor or metastases of a mammary organ of a mammalian host, which comprises:
    combining serum from said host with antibodies bound to a support, wherein said antibodies are specific for at least one surface antigen specific for a normal differentiated epithelial cell of said mammary organ, wherein any of said surface antigen in said serum binds to said antibodies to form an antigen-antibody complex;
    labelling said complex with a label;
    releasing labelled surface antigen from said labelled complex; and
    characterizing said labelled antigen in comparison to known surface antigen.

12. A method for determining the presence of neoplastic tissue from a solid tumor or metastasis of a mammary organ of a mammalian host, which comprises:
    monitoring the level of at least one surface antigen specific for normal differentiated epithelial cells of said mammary organ in the serum of said host.

13. A kit for monitoring the level of a surface antigen specific for a normal differentiated epithelial cell of a mammary organ of a mammalian host which comprises:
    in a container lyophilized antibodies specific for said surface antigen formulated with sufficient amounts of buffer, inert protein and preservatives for use with a blood or plasma sample.

14. A kit according to claim 13, wherein said antibodies are bound to a solid support.

15. A kit according to any of claim 13 or 14, wherein said antibodies are labelled.

16. A kit according to claim 15, wherein the label is a radionuclide.

* * * * *